(12) United States Patent  (10) Patent No.: US 9,745,281 B2
Boiteau  (45) Date of Patent: Aug. 29, 2017

(54) METHOD FOR THE SYNTHESIS OF 4-(HETEROCYCLOALKYL)-BENZENE-1,3,-DIOL COMPOUNDS

(71) Applicant: GALDERMA RESEARCH & DEVELOPMENT, Biot (FR)

(72) Inventor: Jean-Guy Boiteau, Valbonne (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/767,762

(22) PCT Filed: Feb. 14, 2014

(86) PCT No.: PCT/FR2014/050312
§ 371 (c)(1),
(2) Date: Aug. 13, 2015

(87) PCT Pub. No.: WO2014/125231
PCT Pub. Date: Aug. 21, 2014

(65) Prior Publication Data
US 2016/0185749 A1    Jun. 30, 2016

Related U.S. Application Data

(60) Provisional application No. 61/764,638, filed on Feb. 14, 2013.

(30) Foreign Application Priority Data

Feb. 14, 2013  (FR) ...................................... 13 51252

(51) Int. Cl.
C07D 335/02   (2006.01)
C07D 309/06   (2006.01)
C07D 309/10   (2006.01)

(52) U.S. Cl.
CPC ......... *C07D 335/02* (2013.01); *C07D 309/06* (2013.01); *C07D 309/10* (2013.01)

(58) Field of Classification Search
None
See application file for complete search history.

(56) References Cited

FOREIGN PATENT DOCUMENTS

FR   WO 2010063773 A1 *  6/2010  ........... A61K 8/4973
WO   2010/063773 A1   6/2010

OTHER PUBLICATIONS

International Search Report and Written Opinion dated Apr. 22, 2014 corresponding to International Patent Application No. PCT/FR2014/050312, 10 pages.

English Translation of the International Search Report dated Apr. 22, 2014 corresponding to International Patent Application No. PCT/FR2014/050312, 3 pages.

Nitta, A., et al.,"(3R)-3-Amino-4-(2,4,5-trifluorophenyl)-N-{4-[6-(2-methoxyethoxy)benzothialzol-2-yl]tetrahydropyran-4-yl}butanamide as a potent dipeptidyl peptidase IV inhibitor for the treatment of type 2 diabetes," Bioorganic & Medicinal Chemistry Letters, Pergamon, Amsterdam, NL, vol. 18, No. 20, Oct. 2008, pp. 5435-5438.

\* cited by examiner

*Primary Examiner* — Heidi Reese
(74) *Attorney, Agent, or Firm* — Dentons US LLP

(57) ABSTRACT

A method is described for the synthesis of 4-(heterocycloalkyl)-benzene-1,3-diol compounds of general formulae (I) and (II):

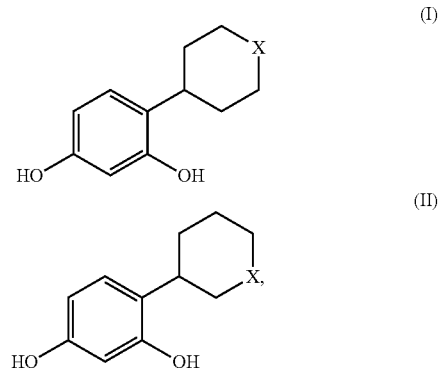

wherein X can be an oxygen atom or a sulphur atom. Also described, is a method for the synthesis of the reactive intermediates of general formula (7a) or (7b)

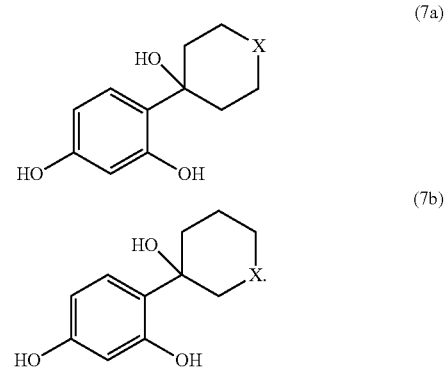

Novel compounds as synthesis intermediates are also described.

38 Claims, 1 Drawing Sheet

METHOD FOR THE SYNTHESIS OF 4-(HETEROCYCLOALKYL)-BENZENE-1,3,-DIOL COMPOUNDS

CROSS-REFERENCE TO PRIOR APPLICATIONS

This application is a National Stage of PCT/FR2014/050312, filed Feb. 14, 2014, and designating the United States (published on Aug. 21, 2014, as WO 2014/125213 A1), which claims priority under 35 U.S.C. §119 to U.S. Provisional Patent Application No. 61/764,638, filed Feb. 14, 2013, and French Patent Application No. 1351252, filed Feb. 14, 2013, each hereby expressly incorporated by reference in its entirety and each assigned to the assignee hereof.

The present invention relates to a process for the synthesis of 4-(heterocycloalkyl)-benzene-1,3-diol compounds corresponding to the following general formulae (I) and (II):

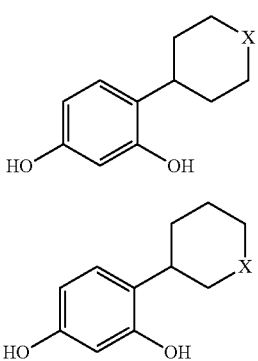

wherein X is an oxygen atom or a sulphur atom.

The synthesis of compounds similar to those of the formulae (I) and (II) above was described in the patent application WO 2010/063773. Said synthesis is carried out in three steps (FIGS. 1 and 2).

In the first step of the process described in the patent application WO 2010/063773 (FIGS. 1 and 2), 2,4-dihydroxybromobenzene (1) is reacted with benzyl bromide to yield the 2,4-dibenzyloxybromobenzene (2).

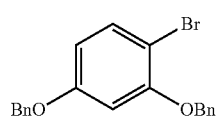

The 2,4-dibenzyloxybromobenzene (2) then is reacted, in the presence of butyllithium, with the heterocycloalkanones of general formula (3a) or (3b) (FIGS. 1 and 2) to yield the benzylic alcohols of the general formula (4a) or (4b), respectively.

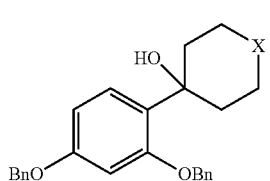

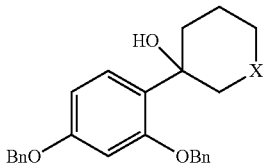

The compounds of the general formulae (I) and (II)

are finally obtained from the compounds of general formulae (4a) and (4b), respectively, by hydrogenation in methanol in the presence of hydrogen and of a palladium-based catalyst.

A first disadvantage of said process is the introduction of a sequence of protection/deprotection reactions of phenols by benzyl groups. Indeed, the need to protect the phenol functional groups of the compound (1) leads, firstly, to the addition of two steps in the synthesis of the compounds (I) and (II) and, secondly, to an unnecessary increase in the mass of the intermediates (2), (4a) or (4b), which is not suitable from an industrial point of view, in particular in terms of the economical use of atoms.

Moreover, said synthesis employs benzyl bromide, whose lachrymatory properties make it tricky to handle on an industrial scale.

A second disadvantage of said synthetic pathway is the use, in the second step, of cryogenic conditions (butyllithium, about −70° C.), which require suitable industrial equipment and, consequently, which makes said process more expensive.

Lastly, a third disadvantage of said process is the high price of 2,4-dihydroxybromobenzene and of butyllithium.

In the context of the development of said compounds, there is a need to have a method for preparing, economically and under safe conditions, the compounds of general formula (I) or (II) while avoiding the disadvantages mentioned above.

The present invention thus aims at solving the problems cited above by proposing a process for the synthesis of the 4-(heterocycloalkyl)-benzene-1,3-diol of general formula (I) or (II) with fewer steps, greater economy, greater simplicity and an ability be adapted to an industrial scale.

The subject matter of the present invention relates to a process for the synthesis of a 4-(heterocycloalkyl)-benzene-1,3-diol corresponding to the general formula (I)

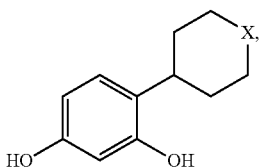

wherein X is an oxygen atom or a sulphur atom, characterized in that a compound corresponding to the general formula (7a)

(7a)

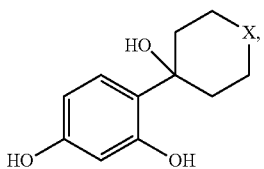

reacts, when X is an oxygen atom, with hydrogen in the presence of a palladium-based catalyst in polar solvent or, when X is a sulphur atom, with a reducing agent of the silicon hydride type and a Lewis acid in nonpolar solvent. Preferably, X is an oxygen atom.

Another subject matter of the invention relates to a process for the synthesis of a 4-(heterocycloalkyl)-benzene-1,3-diol corresponding to the general formula (II)

(II)

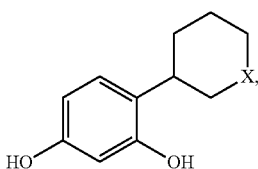

wherein X is an oxygen atom or a sulphur atom, characterized in that a compound corresponding to the general formula (7b)

(7b)

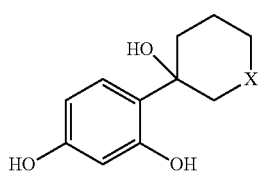

reacts, when X is an oxygen atom, with hydrogen in the presence of a palladium-based catalyst in polar solvent or, when X is a sulphur atom, with a reducing agent of the silicon hydride type and a Lewis acid in nonpolar solvent.

Preferably, the polar solvent used in the two processes above is selected from the group comprising alcohols such as methanol, for example, carboxylic acids such as acetic acid, for example, esters such as ethyl acetate, for example, ethers such as tetrahydrofuran, for example, water, and a mixture of said solvents. Advantageously, the alcohols are selected from methanol, ethanol and isopropanol.

Preferably, the non-polar solvent is selected from the group consisting of dichloromethane and dichloro-1,2-ethane.

Preferably, the palladium-based catalyst is selected from the group consisting of palladium on carbon, palladium hydroxide and palladium acetate.

Preferably, the hydrogen pressure applied in the processes of the invention is between 1 bar and 10 bar.

In another particular embodiment, the compound corresponding to the general formula (7a)

(7a)

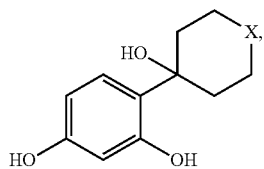

wherein X is an oxygen atom or a sulphur atom, is obtained by reaction of resorcinol with a heterocycloalkanone corresponding to the general formula (3a)

(3a)

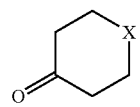

in polar solvent and in the presence of a base.

In another particular embodiment, the compound corresponding to the general formula (7b)

(7b)

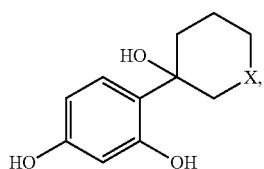

wherein X is an oxygen atom or a sulphur atom, is obtained by reaction of resorcinol with a heterocycloalkanone corresponding to the general formula (3b)

(3b)

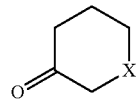

in polar solvent and in the presence of a base.

Preferably, the base is selected from the group comprising sodium hydroxide, potassium hydroxide, lithium hydroxide and metal alcoholates, preferably sodium methanolate and potassium tert-butylate. Advantageously, the base is sodium hydroxide or potassium hydroxide.

Preferably, the polar solvent is selected from the group comprising water and alcohols, preferably methanol, ethanol, and isopropanol. Advantageously, the polar solvent is water.

Preferably, the resorcinol and the heterocycloalkanone (3a) or (3b) are used in a resorcinol/heterocycloalkanone molar ratio between 1 and 8.

Another subject matter of the invention relates to the compound of general formula (7a) or (7b)

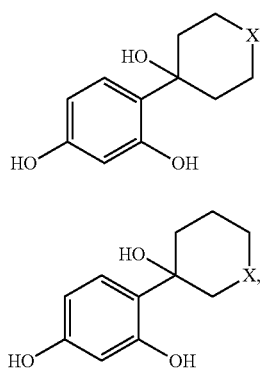

(7a)

(7b)

wherein X is an oxygen atom or a sulphur atom. Preferably the compound is selected from the group consisting of 4-(4-hydroxy-tetrahydro-pyran-4-yl)-benzene-1,3-diol and 4-(3-hydroxy-tetrahydro-pyran-3-yl)-benzene-1,3-diol.

The novel process for the synthesis of the 4-(heterocycloalkyl)-benzene-1,3-diol (I) or (II) of the invention, as illustrated in FIGS. 3 and 4, has the advantage of being a short synthesis comprising at most one linear sequence of two steps.

Said novel synthetic pathway uses the resorcinol (6) as the starting product, which is very advantageous economically compared with the price of the 2,4-dihydroxybromobenzene (1).

The first step of said novel synthetic pathway is a novel step of coupling the resorcinol (6) with the heterocycloalkanones (3a) or (3b) in the presence of a base. The base used is preferably selected from the group comprising sodium hydroxide, potassium hydroxide, lithium hydroxide, and metal alcoholates such as sodium methanolate or potassium tert-butylate, for example. Said step is carried out in polar solvent, preferably in water or in alcohols, and, respectively, produces the compounds (7a) or (7b) directly. The alcohols are preferably selected from the group comprising methanol, ethanol and isopropanol.

During said first step, excess resorcinol (6) is preferably used to react on the heterocycloalkanone (3a) or (3b). More specifically, the resorcinol/heterocycloalkanone molar ratio is between 1 and 8, preferably between 2 and 4.

The temperature at which said coupling step is carried out is another advantage of said novel synthetic pathway. Indeed, said first step is carried out at room temperature, in water or in alcohols, which avoids the cryogenic step (about -70° C.) of the process disclosed in WO 2010/063773. Furthermore, the reaction intermediates (7a) or (7b) are obtained in crystalline form after neutralisation of the medium, thus avoiding the need for purification steps. Therefore, separation on a chromatography column to isolate the reaction intermediates (7a) or (7b)

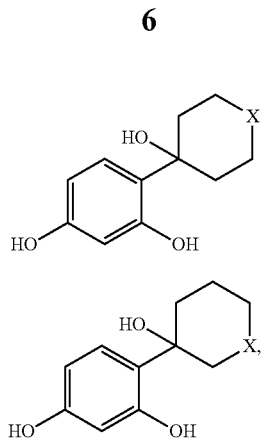

(7a)

(7b)

is not necessary, which is another advantage for the adaptation of said process to an industrial scale. It is preferable to have a pH equal to 7 or a pH of 7 to 8. Preferentially, the pH is equal to 7.

The second step of said novel synthetic pathway is a step of hydrogenation or reduction of the intermediates (7a) or (7b) in order to obtain the compounds of formula (I) or (II), respectively.

If X is an oxygen atom, the hydrogenation of the intermediates (7a) or (7b) is carried out in polar solvent. The preferred polar solvents are selected from the group comprising alcohols such as methanol, for example, carboxylic acids such as acetic acid, for example, esters such as ethyl acetate, for example, ethers such as tetrahydrofuran, for example, water, and a mixture of said solvents. The alcohols are preferably selected from the group comprising methanol, ethanol and isopropanol.

Hydrogenation is carried out in the presence of a palladium-based catalyst. The preferred catalysts are selected from the group consisting of palladium on carbon, palladium hydroxide, palladium acetate, or any other reduction catalyst known to the skilled person. The hydrogen pressure applied is between 1 bar and 10 bar, preferably between 3 bar and 7 bar.

If X is a sulphur atom, the reduction of the intermediates (7a) or (7b) is carried out in nonpolar solvent. The preferred nonpolar solvents are selected from the group comprising dichloromethane and dichloro-1,2-ethane. The reduction is carried out in the presence of a reducing agent of the silicon hydride type and a Lewis acid. The preferred reducing agents are selected from the group consisting of triethylsilane, polymethylhydrosiloxane (PMHS), and any other silicon hydride known to the skilled person. The preferred Lewis acids are selected from the group consisting of boron trifluoride and complexes thereof, such as trifluoroborane etherate, for example.

EXAMPLES

Figure 1:
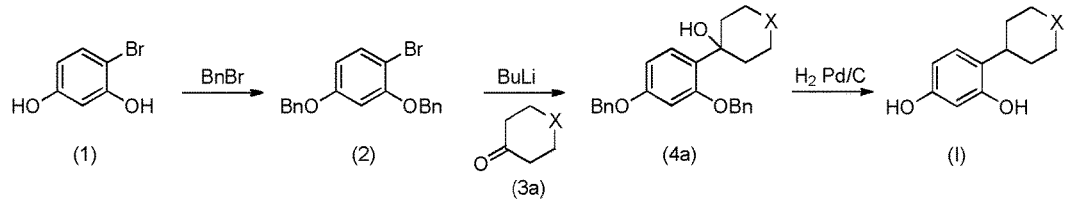
FIG. 1: Preparation of compounds of formula (I) described in WO 2010/063773
Figure 2:
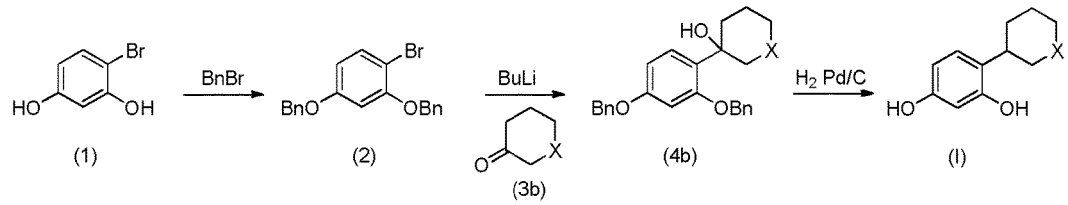
FIG. 2: Preparation of compounds of formula (II) described in WO 2010/063773
Figure 3:
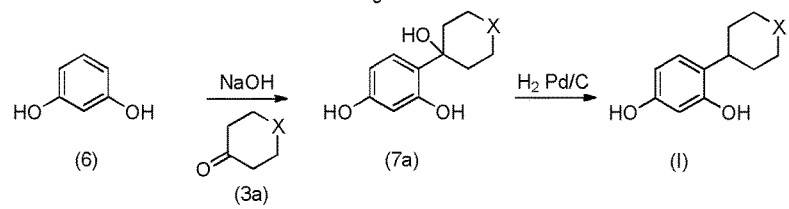
FIG. 3: Process for the preparation of the compounds of the invention of formula (I)
Figure 4:
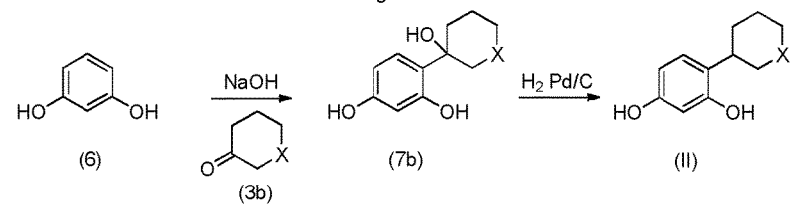
FIG. 4: Process for the preparation of the compounds of the invention of formula (II)

The following examples are now presented in order to illustrate the process as described above. Said examples which illustrate the process of the invention are not limiting.

Example 1

When X=O:
4-(Tetrahydro-pyran-4-yl)-benzene-1,3-diol a) 4-(4-Hydroxy-tetrahydro-pyran-4-yl)-benzene-1,3-diol In a 6-liter double-walled reactor, 550 g (5 mol, 4 eq) of resorcinol is loaded under nitrogen and then 1530 ml of 3 M sodium hydroxide solution is added while maintaining the temperature at 17° C. 125 g of tetrahydro-4-pyranon-4-one (1.25 mol, 1 eq) is added to the reaction mixture. The mixture is then stirred for 2 hours at room temperature and the progress of the reaction is checked using TLC plates (eluent: 2:1 heptane/AcOEt). The reaction is quenched by adding 2 M hydrochloric acid solution until a pH=7 (pH meter) is obtained. 830 g of NaCl is then added and the reaction mixture is stirred overnight at room temperature. The solid is filtered and then washed three times with 1 liter of water. The solid is drained and then dried under a vacuum at 50° C. overnight to yield 125 g of 4-(4-hydroxy-tetrahydro-pyran-4-yl)-benzene-1,3-diol as a crystalline white powder. Yield=48%.
MP=152° C.
$^1$H NMR (DMSO D6, 400 MHz): 1.50 (m, 2H); 2.21 (m, 2H); 3.69 (m, 4H); 5.50 (br s, 1H); 6.20 (m, 2H); 7.16 (d, J=8 Hz, 1H); 6.82 (d, J=8.4 Hz, 1H); 8.95 (s, 1H); 9.11 (br s, 2H).

b) 4-(Tetrahydro-pyran-4-yl)-benzene-1,3-diol 100 g (0.47 mol) of 4-(4-hydroxy-tetrahydro-pyran-4-yl)-benzene-1,3-diol and then 100 ml of acetic acid and 10 g of 10% palladium on carbon are placed in a Parr reactor under nitrogen. 400 ml of THF is added and the reaction mixture is stirred for 5 hours under 5 bar of hydrogen at room temperature. The solution is then filtered on Clarcel, the Clarcel is washed with 250 ml of THF and then the filtrate is concentrated until a final volume of 150 ml is obtained. 50 ml of ethyl acetate is then added and the reaction mixture is stirred for 1 hour at 0° C. The solid is filtered, washed with an additional 50 ml of ethyl acetate and then dried under a vacuum to yield 84 g of 4-(tetrahydro-pyran-4-yl)-benzene-1,3-diol as a crystalline product. Yield=92%.
MP=223° C.
$^1$H NMR (DMSO D6, 400 MHz): 1.54 (m, 4H); 2.92 (m, 1H); 3.39 (m, 2H); 3.90 (m, 2H); 6.14 (dd, J=8.4 and 2.4 Hz, 1H); 6.25 (d, J=2.4 Hz, 1H); 6.82 (d, J=8.4 Hz, 1H); 8.95 (s, 1H); 9.11 (s, 1H).
$^{13}$C NMR (DMSO D6, 100 MHz): 32.6, 33.5, 67.7, 102.3, 106.0, 122.4, 126.7, 155.2, 156.0.

Example 2

When X=S:
4-(Tetrahydro-thiopyran-4-yl)-benzene-1,3-diol a) 4-(4-Hydroxy-tetrahydro-thiopyran-4-yl)-benzene-1,3-diol 13.43 g (0.115 mol, 1 eq) of tetrahydro-thiopyran-4-one suspended in 100 ml of water is added to a degassed mixture of 25.45 g (0.231 mol, 2.0 eq) of resorcinol solubilised in 115 ml (0.231 mol, 2.0 eq) of 2 N sodium hydroxide. The reaction mixture is stirred at room temperature for 2.5 hours. The reaction mixture is treated with 100 ml of 2 N hydrochloric acid solution (pH 5) and extracted with ethyl acetate. The organic phases are combined, dried over magnesium sulphate, filtered and evaporated. 40.88 g of yellow oil is obtained.

Said oil is solubilised in 1 liter of dichloromethane and employed in the following step.

b) 4-(Tetrahydro-thiopyran-4-yl)-benzene-1,3-diol 55 ml (0.345 mol, 3 eq) of triethylsilane and then 44 ml (0.345 mol, 3 eq) of trifluoroborane etherate are added dropwise to a solution (0.115 mol, 1 eq) of crude 4-(4-hydroxy-tetrahydro-thiopyran-4-yl)-benzene-1,3-diol as obtained in the preceding step in 1 liter of dichloromethane. The reaction mixture is stirred at room temperature for 10 minutes. 400 ml of water is added to the reaction mixture followed by 250 ml of saturated sodium bicarbonate solution. The mixture is decanted and the aqueous phase is extracted with dichloromethane. The organic phases are combined, washed with water, dried over magnesium sulphate and concentrated. The insoluble material is filtered. 6.85 g of 4-(tetrahydro-thiopyran-4-yl)-benzene-1,3-diol is obtained as a white powder. Yield=28% from the two steps
MP=171° C.
$^1$H NMR (DMSO D6, 400 MHz): 1.61 (m, 2H); 1.92 (m, 2H); 2.55 (m, 2H), 2.72 (m, 3H); 6.14 (dd, J=8.4 and 2.4 Hz, 1H); 6.25 (d, J=2.4 Hz, 1H); 6.80 (d, J=8.4 Hz, 1H); 8.95 (s, 1H); 9.10 (s, 1H).
$^{13}$C NMR (DMSO D6, 100 MHz): 28.7, 33.8, 35.6, 102.3, 106.0, 123.5, 126.7, 154.8, 156.0.

Example 3

When X=O: 4-(3-Hydroxy-tetrahydro-pyran-3-yl)-benzene-1,3-diol a) 4-(3-Hydroxy-tetrahydro-pyran-3-yl)-benzene-1,3-diol 2.1 g (0.02 mol, 1 eq) of dihydro-pyran-3-one in solution in 2 ml of water is added dropwise to a degassed mixture of 8.8 g (0.08 mol, 4.0 eq) of resorcinol solubilised in 25 ml (0.075 mol, 3.7 eq) of 3 N sodium hydroxide. The reaction mixture is stirred at room temperature for 1 hour. The reaction mixture is treated with 5 ml of concentrated hydrochloric acid solution (pH 7) and then 9 g of sodium chloride is added. The mixture is cooled in an ice bath and extracted with ethyl acetate. The organic phases are combined, dried over magnesium sulphate, filtered and evaporated. The residue is chromatographed on silica gel (AnaLogix SF40-150 g, Spot II column) and eluted with 80:20 and then 20:80 heptane/ethyl acetate. 2.91 g of 4-(3-hydroxy-tetrahydro-pyran-3-yl)-benzene-1,3-diol is obtained as a white amorphous solid. Yield=69% b) 4-(Tetrahydro-pyran-3-yl)-benzene-1,3-diol

A mixture of 2.9 g (0.14 mol, 1 eq) of 4-(3-hydroxy-tetrahydro-pyran-3-yl)-benzene-1,3-diol in 60 ml of ethyl acetate and 6 ml of methanol in the presence of 580 mg (20% by weight) of 10% palladium on carbon is stirred under 5 bar of hydrogen at room temperature for 5 hours and then heated at 50° C. for 24 hours (formation of 10% of the product). 580 mg (20% by weight) of 10% palladium on carbon is added and the reaction mixture is heated at 60° C. under 5 bar of hydrogen for 6 days. 580 mg (20% by weight) of 10% palladium on carbon is added and the reaction mixture is heated at 60° C. under 5 bar of hydrogen for 24 hours. The reaction mixture is filtered on filter paper and the filtrate is evaporated. The residue is chromatographed on silica gel (AnaLogix SF40-150 g, Spot II column) and eluted with 78:22 to 50:50 heptane/ethyl acetate. The oil obtained is crystallised in dichloromethane/heptane, filtered and dried under a vacuum at 40° C. 1.21 g of 4-(tetrahydro-pyran-3-yl)-benzene-1,3-diol is obtained as a white solid. (MP=148-149° C.). Yield=44%

$^1$H NMR (DMSO D6, 400 MHz): 1.54-1.77 (m, 4H); 2.94 (m, 1H); 3.12 (t, J=10.6 Hz, 1H); 3.30 (m, 1H), 3.75 (m, 1H); 3.81 (d, J=11 Hz, 1H); 6.15 (dd, J=8.4 and 2.4 Hz, 1H); 6.26 (d, J=2.4 Hz, 1H); 6.84 (d, J=8.4 Hz, 1H); 9.00 (s, 1H); 9.18 (s, 1H).

$^{13}$C NMR (DMSO D6, 100 MHz): 26.2; 28.8; 34.9; 67.2; 72.1; 102.3; 106.0; 119.0; 127.3; 155.6; 156.4.

The invention claimed is:

1. A method of synthesizing a 4-(heterocycloalkyl)-benzene-1,3-diol corresponding to general formula (I)

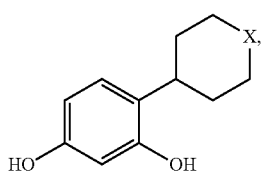

(I)

in which X is an oxygen atom or a sulphur atom, the method comprising reacting a compound corresponding to general formula (7a)

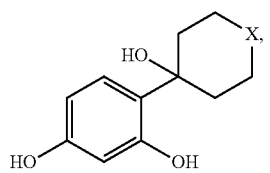

(7a)

when X is an oxygen atom, with hydrogen in the presence of a palladium-based catalyst in polar solvent or, when X is a sulphur atom, with a reducing agent of a silicon hydride type and a Lewis acid in nonpolar solvent.

2. A method of synthesizing a 4-(heterocycloalkyl)-benzene-1,3-diol corresponding to general formula (II)

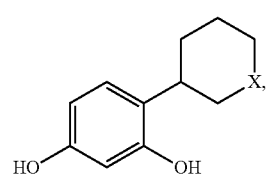

(II)

in which X is an oxygen atom or a sulphur atom, the method comprising reacting a compound corresponding to general formula (7b)

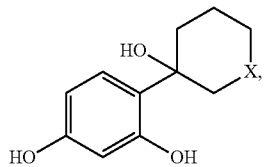

(7b)

when X is an oxygen atom, with hydrogen in the presence of a palladium-based catalyst in polar solvent or, when X is a sulphur atom, with a reducing agent of a silicon hydride type and a Lewis acid in nonpolar solvent.

3. The method according to claim 1, wherein the polar solvent is selected from the group consisting of alcohols, carboxylic acids, esters, ethers, water, and a mixture thereof.

4. The method according to claim 3, wherein the alcohols are selected from the group consisting of methanol, ethanol and isopropanol.

5. The method according to claim 1, wherein the nonpolar solvent is dichloromethane or dichloro-1,2-ethane.

6. The method according to claim 1, wherein the palladium-based catalyst is selected from the group consisting of palladium on carbon, palladium hydroxide and palladium acetate.

7. The method according to claim 1, wherein the hydrogen pressure applied is from 1 bar to 10 bar.

8. The method according to claim 1, wherein the compound corresponding to the general formula (7a)

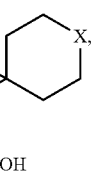

(7a)

is obtained by reacting resorcinol with a heterocycloalkanone corresponding to general formula (3a)

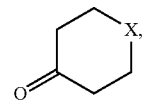

(3a)

in polar solvent and in the presence of a base.

9. The method according to claim 2, wherein the compound corresponding to the general formula (7b)

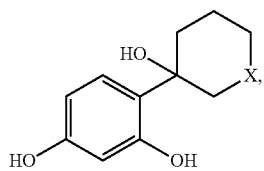

(7b)

is obtained by reacting resorcinol with a heterocycloalkanone corresponding to general formula (3b)

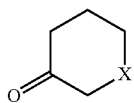
(3b)

in polar solvent and in the presence of a base.

10. The method according to claim 8, wherein the base is selected from the group consisting of sodium hydroxide, potassium hydroxide, lithium hydroxide and metal alcoholates.

11. The method according to claim 10, wherein the base is sodium hydroxide or potassium hydroxide.

12. The method according to claim 8, wherein the polar solvent is selected from the group consisting of water and alcohols.

13. The method according to claim 12, wherein the polar solvent is water.

14. The method according to claim 8, wherein the resorcinol and the heterocycloalkanone (3a) is used in a resorcinol/heterocycloalkanone molar ratio of from 1 to 8.

15. A compound of general formula (7a) or (7b)

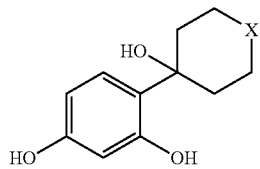
(7a)

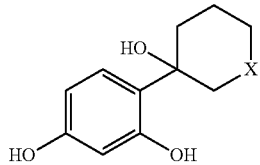
(7b)

wherein X is an oxygen atom or a sulphur atom.

16. The compound according to claim 15, wherein the compound is 4-(4-hydroxy-tetrahydro-pyran-4-yl)-benzene-1,3-diol or 4-(3-hydroxyl-tetrahydro-pyran-3-yl)-benzene-1,3-diol.

17. The method according to claim 1, wherein X is an oxygen atom.

18. The method according to claim 2, wherein the polar solvent is selected from the group consisting of alcohols, carboxylic acids, esters, ethers, water, and a mixture thereof.

19. The method according to claim 2, wherein the non-polar solvent is dichloromethane or dichloro-1,2-ethane.

20. The method according to claim 2, wherein the palladium-based catalyst is selected from the group consisting of palladium on carbon, palladium hydroxide and palladium acetate.

21. The method according to claim 2, wherein the hydrogen pressure applied is from 1 bar to 10 bar.

22. The method according to claim 9, wherein the base is selected from the group consisting of sodium hydroxide, potassium hydroxide, lithium hydroxide and metal alcoholates.

23. The method according to claim 9, wherein the polar solvent is selected from the group consisting of water and alcohols.

24. The method according to claim 9, wherein the resorcinol and the heterocycloalkanone (3b) is used in a resorcinol/heterocycloalkanone molar ratio of from 1 to 8.

25. The method according to claim 3, wherein when the polar solvent is alcohol, the alcohol is methanol.

26. The method according to claim 3, wherein when the polar solvent is a carboxylic acid, the carboxylic acid is acetic acid.

27. The method according to claim 3, wherein the polar solvent is an ester, the ester is ethyl acetate.

28. The method according to claim 3, wherein the polar solvent is an ether, the ether is tetrahydrofuran.

29. The method according to claim 18, wherein the alcohols are selected from the group consisting of methanol, ethanol and isopropanol.

30. The method according to claim 22, wherein the base is sodium hydroxide or potassium hydroxide.

31. The method according to claim 23, wherein the polar solvent is water.

32. The method according to claim 10, wherein the base is sodium methanolate or potassium tert-butylate.

33. The method according to claim 22, wherein the base is sodium methanolate or potassium tert-butylate.

34. The method according to claim 12, wherein when the polar solvent is alcohol, the alcohol is selected from the group consisting of methanol, ethanol and isopropanol.

35. The method according to claim 18, wherein when the polar solvent is alcohol, the alcohol is methanol.

36. The method according to claim 18, wherein when the polar solvent is a carboxylic acid, the carboxylic acid is acetic acid.

37. The method according to claim 18, wherein the polar solvent is an ester, the ester is ethyl acetate.

38. The method according to claim 18, wherein the polar solvent is an ether, the ether is tetrahydrofuran.

* * * * *